United States Patent [19]

Toth et al.

[11] Patent Number: 4,804,379

[45] Date of Patent: Feb. 14, 1989

[54] ABSORBENT PAD WITH MOISTURE BARRIER STRIPS

[75] Inventors: Michael R. Toth, Andover, Mass.; Mary E. Buckley, Wheeling, Ill.

[73] Assignee: The Kendall Company, Boston, Mass.

[21] Appl. No.: 60,125

[22] Filed: Jun. 9, 1987

[51] Int. Cl.4 .............................................. A61F 13/16
[52] U.S. Cl. ................................ 604/378; 604/385.1
[58] Field of Search ........... 604/378, 381, 383, 385 A, 604/385 R, 397, 398

[56] References Cited

U.S. PATENT DOCUMENTS 3,994,299 11/1976 Karami .......................... 604/378 X Primary Examiner—Allen M. Ostrager
Attorney, Agent, or Firm—Donald N. Halgren

[57] ABSTRACT

A disposable absorbent pad for utilization as a diaper or adult brief, comprising an absorbent pad being covered on one side by a sheet of fluid impervious material, and on the other side by a pair of generally parallel strips of fluid impervious material overlapping the absorbent pad and the backing sheet, in the crotch area to prevent leakage of fluid from the absorbent pad in the crotch area.

23 Claims, 4 Drawing Sheets

ABSORBENT PAD WITH MOISTURE BARRIER STRIPS

BACKGROUND OF THE INVENTION (1.) Field of the Invention

This invention relates to absorbent pads and more particularly to incontinent briefs and disposable diapers having waterproof crotch seals.

2. Description of the Prior Art

Minimization of leakage of diapers has been long sought after. A more notable patent in that area is shown in Buell, U.S. Pat. No. 3,860,003. In that patent elastic strips are secured to the crotch portions of the diaper and spaced at least three quarters of an inch from the absorbent pad to form elasticized crotch seals for securement over the legs of an infant to prevent loss of fluid from the interior of the diaper along the legs of the infant.

A more recent patent concept is shown in U.S. Pat. No. 4,643,728 to Karami. This patent shows a disposable diaper having elasticized waterproof crotch seals formed from waterproof elastic strips secured to the backing sheet and the absorbent pad and which strips are under tension to eliminate transverse pleats in the crotch area.

Other patents of interest, showing sealing means are U.S. Pat. No. 4,585,447 to Karami and U.S. Pat. No. 4,585,449 to Karami.

BRIEF SUMMARY OF THE INVENTION

The present invention improves upon the prior art diapers. The present invention includes a generally hourglass shaped brief or diaper having a crotch area and portions of greater width defining ears. The absorbent pad or brief comprises a backing sheet of fluid impervious film. The pad may also comprise a top sheet of nonwoven fibers or the like. The backing sheet may be sealed to the top sheet along the peripheral edges thereof by heat or adhesive means. An absorbent pad is disposed between the top sheet and the backing sheet. The pad may generally conform to an hourglass shape. A moisture proof barrier is disposed to cover the sides of the absorbent pad and adjacent to part of the top sheet.

An elongated strip of fluid impervious material, having generally parallel side portions, has one side portion secured to the backing sheet in the crotch area and its other side portion overlying the pad, the strip extending generally parallel to the longitudinal axis of the brief, on each side thereof, adjacent the leg cut-out areas which between them, define the crotch area. The moisture proof barrier forms a wall or dam to prevent leakage of any fluids contained between the backing sheet and the barrier. Thus it is shown that the absorbent pad with the barrier can contain the liquids absorbed therein and prevent those liquids from extending around the crotch portion and leak from the ears of the absorbent pad.

DETAILED DESCRIPTION OF THE PREFERRED EMBODIMENT

Figure 1:
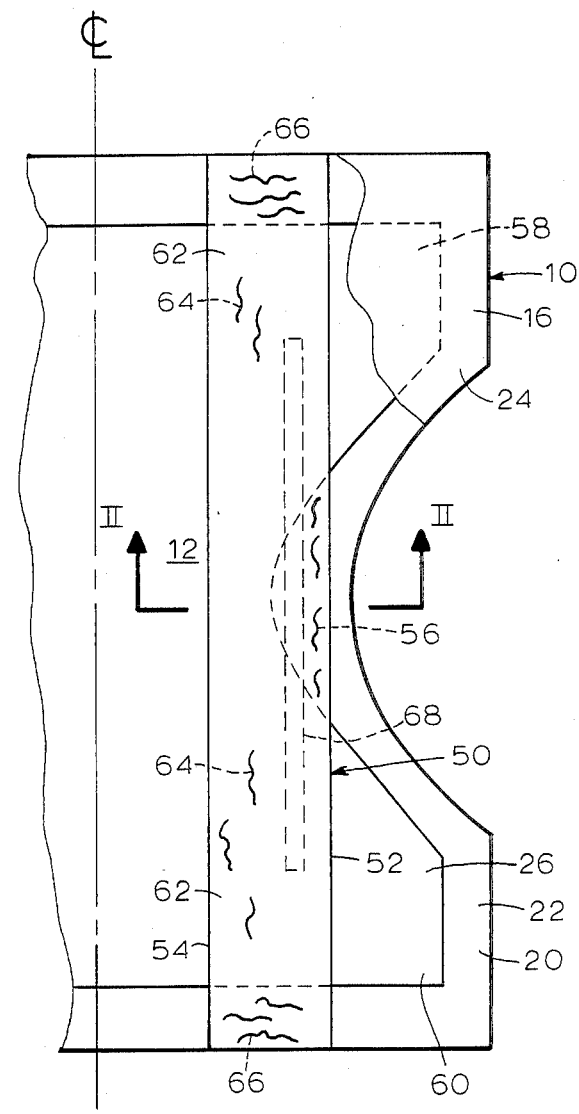
FIG. 1 is a fragmentary plan view of the diaper constructed according to the principles of the present invention.
Figure 2:
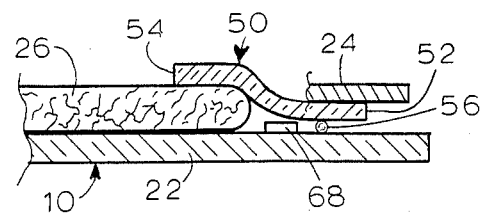
FIG. 2 is a sectional view taken substantially as indicated along the line II—II of FIG. 1.

Referring now the drawings in detail and particularly to FIGS. 1 and 2, there is shown a contoured disposable absorbent pad 10 such as an incontinent brief or diaper, constructed in accordance with the principles of the present invention. The absorbent pad 10 of a generally hourglass configuration with only one-half being shown, to the right of the center line, and has a crotch area 12 and four portions of greater width each comprising only ears 16 and 20 being shown. The pad 10 includes a backing sheet 22 of a fluid impervious sheet such as polyethylene or polypropylene film. A top sheet 24, preferably of nonwoven or polyethylene or polypropylene fibers is preferably heat sealed by heat or hot melt lines, to the backing sheet along the peripheral edges of the absorbent pad. An inner absorbent pad 26 is disposed between the top sheet 24 and backing sheet 22 and may be made of wood fluff or like absorbent. The inner pad 26 may conform generally to an hourglass configuration.

Figure 3:
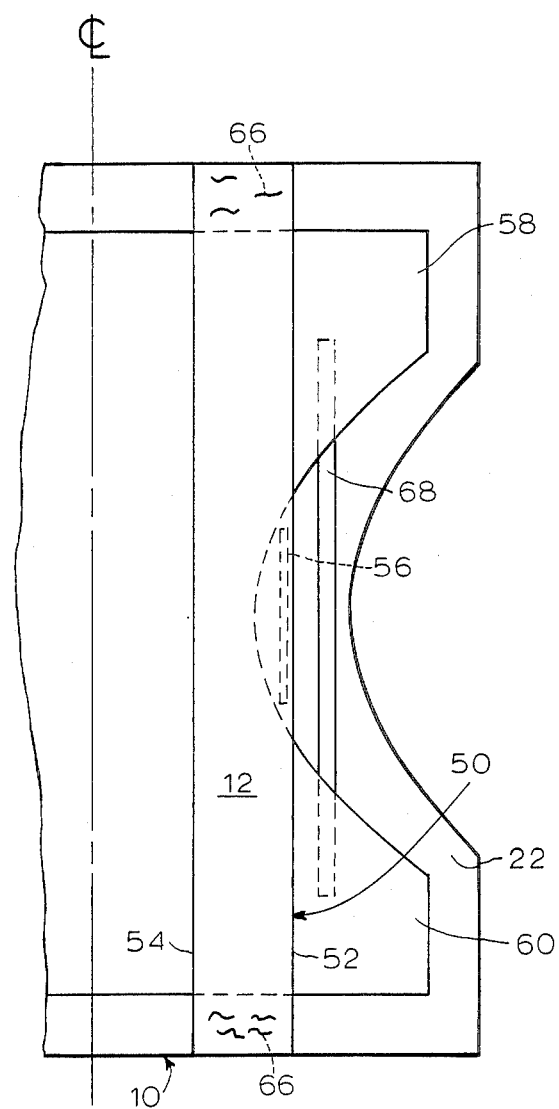
FIG. 3 is a fragmentary plan view of another embodiment of the diaper of the present invention.

The pad 10 has an elongated strip 50 constructed from a suitable fluid impervious material, such as polyethylene, having generally parallel opposed side edges 52 and 54, with the strip 50 extending between opposed ends of the pad 10. In the crotch area 12, a normal line of adhesive 56 secures a first side portion of the strip 50 to the backing sheet 22, such that the second generally parallel side portion of the strip 50 extends over a side edge of the pad 26, and covers a side portion of the pad 26. In this manner, the strip 50 serves as a waterproof area or dam in the crotch area 12 of the pad 10. The strip 50 extends over the pad 26 with ears 58 and 60 of the pad 26 projecting past the strip 50. Intermediate portions 62 of the strip 50 may be secured to an upper surface of the pad 26 by suitable adhesive 64, or the strip 50 may be free of adhesive in this area. The opposed ends of the strip 50 may be secured to the backing sheet 22 by suitable adhesive 66. A suitable elastic band 68 may be secured to the backing sheet 22 by adhesive in order to gather the crotch area 12 of the pad 10. In this embodiment, the band 68 is located beneath the strip 50. In the embodiment of FIG. 3, the elastic band 68 is located intermediate the strip 50 and a side edge of the backing sheet.

Figure 4:
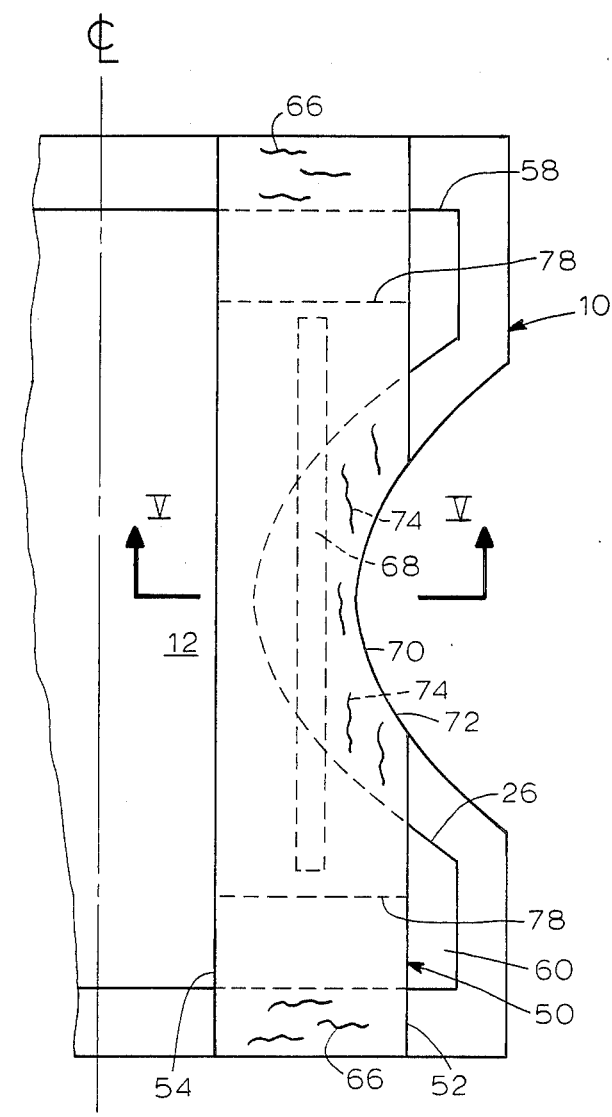
FIG. 4 is a fragmentary plan view of another embodiment of the diaper of the present invention.
Figure 5:
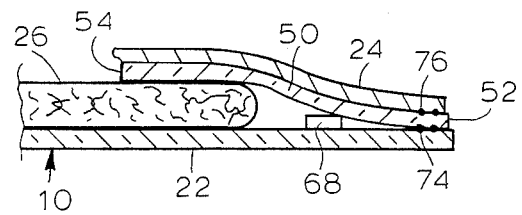
FIG. 5 is a sectional view taken substantially as indicated along the line V—V of FIG. 4.

Another embodiment of the present invention is illustrated in FIGS. 4 and 5, in which like reference numerals designate the pads. In this embodiment, the strip 50 has a greater width than the strip 50 of FIGS. 1 and 2, and extends farther toward the side of the pad 10, although the strip 50 also covers a side portion of the pad 26 in order to serve as a moisture barrier or dam for the pad 26. The strip 50 extends to the side edge 70 of the pad 10 in the crotch area, and has a cut-out 72 in order to conform to the contour of the pad 10 in the crotch area. The strip 50 is secured to the backing sheet 22 by suitable adhesive lines 74 in the crotch area 12, and the top sheet 24 is secured to the strip 50 near the side edge of the pad 10 by suitable adhesive 76 in the crotch area 12. The pad 10 may have an elastic band 68 secured to the backing sheet 22 in the crotch area 12 in a manner as previously described. As shown, the strip 50 may extend to opposed ends of the pad 10, and the ends of the strip 50 may be secured to the backing sheet 22 at opposed ends of the strip 50. Alternatively, the strip may be cut shorter than the length of the pad 10 as shown along dotted lines 78 such that the opposed ends of the strip 50 are spaced from opposed ends of the pad 10.

Figure 6:
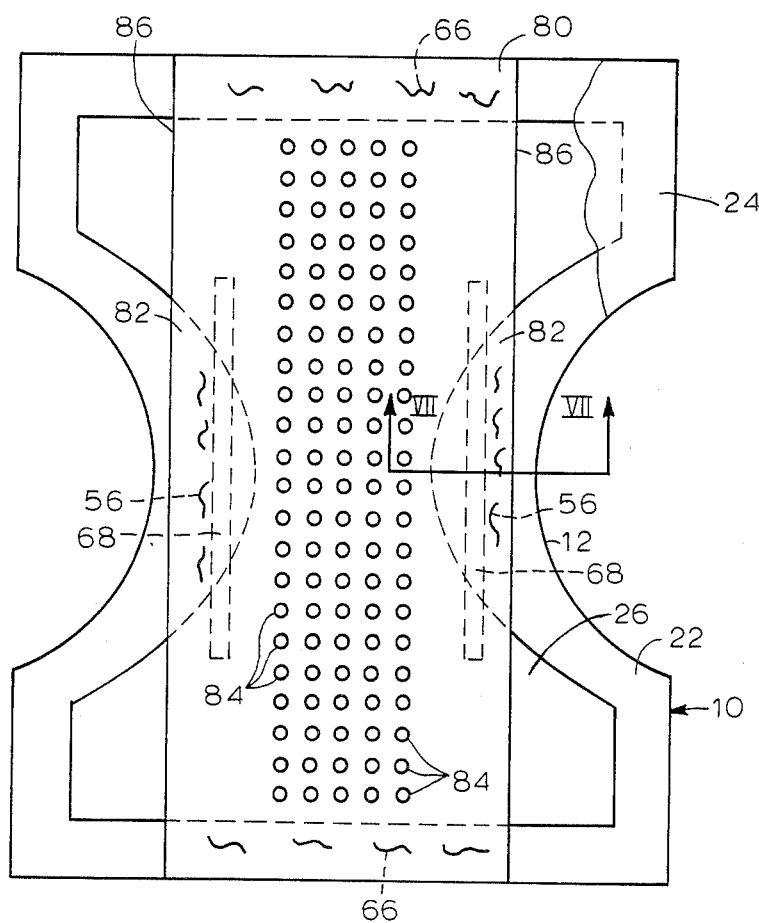
FIG. 6 is a plan view of another embodiment of the diaper of the present invention.
Figure 7:
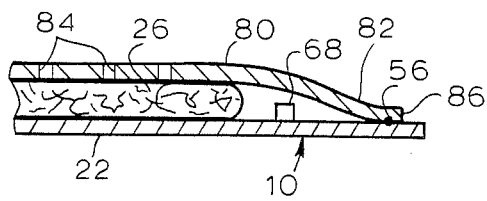
FIG. 7 is a sectional view taken substantially as indicated along the line VII—VII of FIG. 6.

Another embodiment of the pad 10 of the present invention is illustrated in FIGS. 6 and 7, in which like reference numerals designate like parts. In this embodiment, the pad 10 has an elongated sheet 80 of fluid impervious material, similar to Telfa, a trademarked material of the Colgate Palmolive Company, or such as polyethylene, preferably extending to opposed ends of the pad 10, and the opposed ends of the sheet 80 may be secured to the backing sheet 22 by suitable adhesive 66. The sheet 80 extends past the opposed side edges of the pad 26 in the crotch area 12 by normal adhesive lines 56. The sheet 80 has a pluralilty of openings 84 extending therethrough, with the openings 84 being spaced from side edges 86 of the sheet 80 such that the side margins 82 of the sheet 80 serve as waterproof barriers or a dam in the crotch area. As shown, the openings 84 may extend substantially the length of the sheet 80 or may be limited only in the crotch area 12. The ears of the pad 26 may project past the side edges 86 of the sheet 80. The pad 10 may have elastic bands 68 secured to the backing sheet 22 beneath the sheet 80. In use, the openings 84 of the sheet 80 permit passage of liquid through the sheet 80 to the pad 26, while the fluid impervious sheet 80 prevents back wetting of the liquid from the pad 26 to the user.

We claim:

1. A disposable absorbent pad assembly comprising:
a backing sheet of fluid impervious material;
a top sheet of fluid pervious material;
an absorbent pad disposed between the backing sheet and top sheet; and
an elongated strip of fluid impervious material having a side portion secured to the backing sheet in the crotch area of the pad assembly, and an opposed side portion overlying the pad in the crotch area in order to prevent leakage from the pad in the crotch area of the pad assembly.

2. The pad assembly of claim 1 wherein the strip extends to opposed ends of the pad assembly.

3. The pad assembly of claim 2 wherein opposed ends of the strip are secured to the backing sheet adjacent the opposed ends of the pad assembly.

4. The pad assembly of claim 2, wherein the strip is secured to the pad intermediate the crotch area and opposed ends of the pad assembly.

5. The pad assembly of claim 2 wherein the strip is free of attachment to the pad intermediate the crotch area and opposed ends of the pad assembly.

6. The pad assembly of claim 2 wherein the pad has a pair of opposed ears projecting past a side edge of the strip.

7. The pad assembly of claim 1 wherein opposed ends of the strip are spaced from opposed ends of the pad assembly.

8. The pad assembly of claim 1 including an elastic band beneath the strip in the crotch area to produce a gathering of the pad assembly in the crotch area.

9. The pad assembly of claim 1 including an elastic band located between a side edge of the strip and a side edge of the pad assembly to produce a gathering of the pad assembly in the crotch area.

10. The pad assembly of claim 1 wherein the pad has a cut-out in the crotch area.

11. The pad assembly of claim 1 wherein the strip extends to a side edge of the pad assembly in the crotch area.

12. The pad assembly of claim 11 wherein the pad assembly has a cut-out defining a side edge in the crotch area of the pad assembly, and in which the strip has a cut-out defining a side edge of the strip being generally aligned with the side edge of the pad assembly.

13. The diaper of claim 11 wherein the strip is secured to the backing sheet adjacent a side edge of the pad assembly.

14. The diaper of claim 13 wherein the top sheet is secured to the strip adjacent the side edge of the pad assembly.

15. The diaper of claim 1 wherein the strip has a pair of opposed generally parallel side edges.

16. A disposable absorbent pad assembly, comprising a backing sheet of fluid impervious material;
a top sheet of fluid pervious material;
an absorbent pad disposed between the backing sheet and top sheet and an elongated sheet of fluid impervious material disposed intermediate the pad and top sheet, said sheet having lateral side margins extending past opposed side edges of the pad in the crotch area and being secured to the backing sheet in the crotch area, said sheet having a plurality of openings in the crotch area extending therethrough, with the openings being spaced from the side margins of the sheet.

17. The pad assembly of claim 16 wherein the sheet extends to opposed ends of the pad assembly.

18. The pad assembly of claim 16 wherein opposed ends of the sheet are secured to the backing sheet.

19. The pad assembly of claim 17 wherein the openings extend to a location adjacent the opposed ends of the pad assembly.

20. The pad assembly of claim 16 including a pair of elastic bands beneath the sheet and producing a gathering of the pad assembly in the crotch area.

21. The pad assembly of claim 16 wherein the pad has a cut-out in the crotch area.

22. The pad assembly of claim 16 wherein the pad assembly has a cut-out in the crotch area.

23. The pad assembly of claim 16 wherein the pad has a plurality of ears projecting past opposed side edges of the sheet in waistband portions of the pad assembly.

* * * * *